United States Patent [19]

Prokai

[11] 3,952,038

[45] Apr. 20, 1976

[54] POLYETHER URETHANE FOAM
[75] Inventor: Bela Prokai, Mahopac, N.Y.
[73] Assignee: Union Carbide Corporation, New York, N.Y.
[22] Filed: June 3, 1974
[21] Appl. No.: 475,968

Related U.S. Application Data
[63] Continuation-in-part of Ser. No. 325,327, Jan. 22, 1973, abandoned.

[52] U.S. Cl. .................. 260/448.2 N; 260/2.5 AH; 260/448.8 R
[51] Int. Cl.² .................... C07F 7/10; C07F 7/18
[58] Field of Search ............. 260/448.2 N, 448.8 R

[56] References Cited
UNITED STATES PATENTS

| | | | |
|---|---|---|---|
| 2,872,435 | 2/1959 | Speier | 260/448.8 R X |
| 2,957,899 | 10/1960 | Black et al. | 260/448.8 R X |
| 3,026,278 | 3/1962 | Walton et al. | 260/448.2 N X |
| 3,168,544 | 2/1965 | Jex | 260/448.2 N |
| 3,185,663 | 5/1965 | Prober | 260/448.2 N X |
| 3,185,719 | 5/1965 | Prober | 260/448.2 N |
| 3,531,508 | 9/1970 | Goldman et al. | 260/448.2 N |
| 3,629,309 | 12/1971 | Bailey et al. | 260/448.8 R X |

Primary Examiner—Paul F. Shaver
Attorney, Agent, or Firm—Reynold J. Finnegan

[57] ABSTRACT

A process for producing high resilience polyether urethane foam using a cyanoalkyl modified siloxane fluid; the foams derived therefrom; a solvent-solution of said siloxane; and cyanoalkyl modified siloxane fluids per se.

25 Claims, No Drawings

POLYETHER URETHANE FOAM

This application is a continuation in part of U.S. patent Application Ser. No. 325,327 filed Jan. 22, 1973, now abandoned.

BACKGROUND OF THE INVENTION

This invention relates to high resilience polyurethane foams and more particularly to the use of certain organosilicon polymers in the production of such foams.

Basically such high resilience foams are produced by the reaction of highly primary hydroxyl-capped, high molecular weight polyols with organic isocyanates and water. High resilience polyurethane foams are distinguishable in part from conventional hot cure polyurethane foams by the use of such polyols and the fact that high resilience polyurethane foams require little or no oven curing and thus are often referred to as cold cure foams. Such foams are extremely desirable for cushioning applications because of their excellent physical properties, e.g. very high foam resiliency, low flammability, open-celled structure, low flex fatigue (long life) and high SAC factors (load bearing properties).

Because of the high reactivity of high resilience foam ingredients and their rapid buildup of gel strength, sometimes the foam can be obtained without a cell stabilizer, however such foams typically have very irregular cell structure as particularly evidenced by surface voids and the discovery of a proper agent to help control cell structure has remained a major problem in the art.

Attempts to solve this problem with surfactants generally employed in the stabilization of hot cure polyurethane foam have not proven satisfactory because such surfactants tend to overstabilize, causing extremely tight, shrinkaging foam. Nor is the problem corrected by reducing the concentrations of such surfactants, since at concentrations required to eliminate shrinkage, the cells are no longer stabilized satisfactorily and the foam structure becomes irregular, coarse and contains surface voids.

The use of low viscosity dimethylsilicone oils alone as stabilizers for high resilience foams also has various disadvantages. For example, at low concentrations they create metering and pumping problems in the processing of the foam, while at higher concentrations these oils adversely affect the physical properties of the foam. Solvents for such dimethylsiloxane oils that are nonreactive with the foam ingredients e.g. alkanes, hexamethyldisiloxane, and the like, can adversely affect the foam's physical properties in proportion to their concentration and generally create flammability hazards. Furthermore isocyanate reactive diluents, such as polyether triols and the like which do not significantly change the foam's properties, inasmuch as they react into the system and become part of the foam structure, are not satisfactory solvents for dimethylsilicone oils, since not enough oil can be dissolved to provide foam stabilization at practical solution concentrations. High resilience foams are also adversely affected by dimethylsilicones having more than about 10 dimethylsiloxy units per siloxane. For example only 5 or 10 weight per cent of such species in a dimethyl silicone oil can appreciably degrade the foam's physical properties and even cause foam shrinkage.

Moreover, while particularly unique high resilience polyether urethane foam can be prepared employing certain siloxane-oxyalkylene block copolymers as disclosed in U.S. Pat. application Ser. No. 84,181 filed Oct. 26, 1970 now U.S. Pat. No. 3,741,917, or certain aralkyl modified siloxane polymers as disclosed in U.S. Pat. application Ser. No. 305,713 filed Nov. 13, 1972 now U.S. Pat. No. 3,839,384, said disclosures do not teach the use of the novel organosilicon polymers employed in this invention.

SUMMARY OF THE INVENTION

It has been discovered that flexible high resilience polyether urethane foam can be prepared according to the instant invention which involves employing certain novel siloxane polymer fluids as more fully defined below.

The siloxane polymer fluids employed in this invention have been found to control the cell uniformity of high resilience polyether urethane foam without obtaining tight foam and without introducing foam shrinkage or causing any severe adverse effects to the foam's physical properties, e.g. the foam's resilience and its resistance towards flammability. Moreover voids in the foam are eliminated by the instant invention and the cell structure of the foam is also much more uniform and finer than where no stabilizing agent is employed. This discovery is surprising since as outlined above not all surfactants are so suitable for use in the production of high resilience foams. Indeed even siloxane polymer fluids of the same type employed herein, but outside the scope of the instant invention, were found to cause shrinkage of the foam or not to eliminate the voids of the foam.

Therefore it is an object of this invention to provide a process for producing high resilience polyether urethane foam. It is further an object of this invention to provide novel organosilicon fluids for use in said process. It is still another object of this invention to provide novel compositions of said fluids for use in said process. It is also another object of this invention to provide high resilience polyether urethane foams produced by said process. Other objects and advantages of this invention will become readily apparent from the following description and appended claims.

More particularly this invention is directed, in part, to a process for preparing high resilience polyether urethane foam, said process comprising foaming and reacting a reaction mixture comprising:

I. an organic polyol selected from the group consisting of (A) a polyether triol containing at least 40 mole per cent primary hydroxyl groups and having a molecular weight from about 2,000 to about 8,000 and (B) a mixture of said polyether triol and other polyethers having an average of at least two hydroxyl groups, said polyether triol of said mixture amounting to at least 40 weight per cent of the total polyol content;

II. an organic polyisocyanate, said organic polyol and said polyisocyanate being present in the mixture in a major amount and in the relative amount required to produce the urethane;

III. a blowing agent in a minor amount sufficient to foam the reaction mixture;

IV. a catalytic amount of a catalyst for the production of the urethane from the organic polyol and polyisocyanate; and V. a minor amount of a cyanoalkyl modified siloxane fluid having the average formula

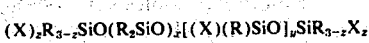

wherein $x$ has a value of 1 to 6 inclusive; $y$ has a value of 0 to 6 inclusive; $z$ has a value of 0 to 1 inclusive; R is a lower alkyl or phenyl radical; and X is a cyanoalkyl radical of the formula

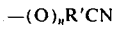

$$-(O)_nR'CN$$

where $n$ has a value of 0 or 1 and R' is an alkylene radical having from 2 to 4 carbon atoms; said siloxane fluid containing at least one of said cyanoalkyl radicals and having an average molecular weight in the range of about 400 to 1500.

It is to be understood of course that the above process and the appended claims read on employing a single ingredient of the type specified or any of the various combinations of ingredient mixtures possible. For example, in addition to employing a single ingredient of the types specified, if desired, a mixture of triols, a mixture of polyisocyanates, a mixture of blowing agents, a mixture of catalysts and/or a mixture of siloxane fluids can be employed. Likewise the triol-polyether starting mixture could consist of a single triol and a mixture of polyethers, a mixture of triols and a single polyether or a mixture of two or more triols and two or more polyethers.

DESCRIPTION OF THE PREFERRED EMBODIMENTS

As indicated above the cyanoalkyl modified siloxane fluid compounds employed as the siloxane stabilizers for cell control in this invention are characterized as having an average molecular weight range, as containing dihydrocarbyl siloxy units ($R_2SiO$) and siloxy units containing a cyanoalkyl radical

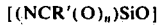

$$[(NCR'(O)_n)SiO]$$

It is of course to be understood that the individual internal siloxy units can be the same or different and can be arranged in any order. Subject to the above qualifications, a more detailed description of the cyanoalkyl modified siloxane fluids is presented below.

Accordingly the siloxane surfactants useful in this invention contain internal dihydrocarbyl siloxy units, such as dimethylsiloxy, diethylsiloxy, dipropylsiloxy, methylethylsiloxy, methylphenylsiloxy groups, and the like. Examples of internal cyanoalkyl siloxy units that can be present in said siloxanes include, e.g. (beta-cyanoethoxy) methylsiloxy, (beta-cyanoethyl) methylsiloxy, (beta-cyanopropyl) methylsiloxy, (gamma-cyanopropyl) methylsiloxy, (gamma-cyanopropyloxy) methylsiloxy, (gamma-cyanopropyl) ethylsiloxy, (delta-cyanobutyl) methylsiloxy, (gamma-cyanobutyl) methylsiloxy, and the like. Illustrative end-blocking or chain terminating siloxy units of said siloxanes are such terminal groups as trimethylsiloxy, triethylsiloxy, (gamma-cyanopropyloxy) dimethylsiloxy, (beta-cyanoethyl) dimethylsiloxy, (beta-cyanopropyl) dimethylsiloxy, (gamma-cyanopropyl) dimethylsiloxy, (delta-cyanobutyl) dimethylsiloxy groups and the like. Preferably R is a methyl radical. Thus illustrative of the more preferred polymeric siloxane fluids employed in the instant invention are trimethyl end-blocked (gamma-cyanopropyloxy) methylsiloxy-dimethylsiloxanes, trimethyl end-blocked (beta-cyanoethyl) methylsiloxy-dimethylsiloxanes, trimethyl end-blocked (beta-cyanopropyl) methylsiloxy-dimethylsiloxanes, trimethyl end-blocked (gamma-cyanopropyl) methylsiloxy-dimethylsiloxanes, trimethyl end-blocked (delta-cyanobutyl) methylsiloxy-dimethylsiloxanes, (gamma-cyanopropyloxy) dimethyl end-blocked dimethylsiloxanes, (beta-cyanoethyl) dimethyl end-blocked dimethylsiloxanes, (beta-cyanopropyl) dimethyl end-blocked dimethylsiloxanes, (gamma-cyanopropyl) dimethyl end-blocked dimethylsiloxanes, (delta-cyanobutyl) dimethyl end-blocked dimethylsiloxanes, trimethyl end-blocked (beta-cyanoethyl) methylsiloxy-(gamma-cyanopropyl) methylsiloxy-dimethylsiloxanes, (gamma-cyanopropyloxy) dimethyl end-blocked-(gamma-cyanopropyloxy) methylsiloxy-dimethylsiloxanes, (beta-cyanoethyl) dimethyl end-blocked-(beta-cyanoethyl) methylsiloxy-dimethylsiloxanes, (beta-cyanopropyl) dimethyl end-blocked-(beta-cyanopropyl) methylsiloxy-dimethylsiloxanes, (gamma-cyanopropyl) dimethyl end-blocked-(gamma-cyanopropyl) methylsiloxy-dimethylsiloxanes, and (delta-cyanobutyl) dimethyl end-blocked-(delta-cyanobutyl) methylsiloxy-dimethylsiloxanes, and the like. Most preferably the cyanoalkyl radical is bonded directly to the silicon atom through one of its carbon atoms, i.e., Si—C instead of through an oxygen atom, i.e., Si—O—C.

Furthermore it is considered that the above cyanoalkyl modified siloxane fluids having an average molecular weight in the range of about 400 to about 1500 employed as the cell stabilizers in this invention are novel compounds per se. The preferred siloxane fluids are those having an average molecular weight range of about 400 to about 900, especially the trimethyl end-blocked (gamma-cyanopropyl) methylsiloxy-dimethylsiloxanes.

The siloxane fluids of this invention can be produced by any number of conventional methods well known in the art, as shown e.g. by U.S. Pat. No. 3,221,040 and U.S. patent application, Ser. No. 279,883 filed Aug. 11, 1972, now U.S. Pat. No. 3,846,462. Preferably the siloxane fluids containing nonhydrolyzable cyanoalkyl radicals (Si—R'CN) are prepared by equilibration of corresponding siloxanes, e.g. hexamethyldisiloxane, cyclic dimethyl siloxane and tetracyclic (gamma-cyanopropyl) methylsiloxane, using an acid or base catalyst. For instance they can be prepared by equilibration using acid catalysts. Anhydrous trifluoromethyl sulfonic acid in concentrations of about 0.1 to 2.0 weight per cent and concentrated sulfuric acid may be employed successfully. The equilibration is generally run at temperatures of about 25° to 50°C. with vigorous stirring at least until the mixture has become homogeneous. Said siloxane fluids can also be prepared by equilibration using a base catalyst, e.g. potassium silanolate, cesium hydroxide and tetramethyl ammonium silanolate. Such catalysts are normally employed in concentrations of 30–200 ppm as potassium equivalent. The equilibration temperature depends on the catalyst employed. For instance, with tetramethyl ammonium silanolate a temperature of about 75° to 100°C. is sufficient, preferably about 85° to 90°C., while the other alkaline catalysts usually require a temperature of at least about 150°C. Generally the equilibration time is less than five hours. Alternatively said siloxane fluids may also be prepared by the platinium catalyzed addition of an olefinic cyanide, e.g. allyl cyanide to the corresponding hydrosiloxane at temperatures of generally about 80° to 90°C. Such platinum catalysts and platinum derivatives are well known in the art, chloroplatinic acid is particularly effective. The platinum catalyst is conveniently employed as a solution for example in tetrahydrofuran, ethanol, butanol or mixed solvents such as ethanol-ethylene glycol dimethyl ether. The general preferred concentration of platinum in the catalyst, based on the total weights of siloxane and olefinic derivatives, is about 5 to 100 parts per million, although higher and lower concentrations may be used. Solvents for the reaction e.g. benzene, toluene, xylene, ethers, and the like can be used if desired. The preferred temperature range for the platinum catalyzed addition process is generally from about 60° to 120°C. Lower temperatures may be used but the reaction times are slower. Higher temperatures may also be used e.g. up to 200°C. but offer no apparent advantage. The choice of solvent if used should of course be adapted to the preferred temperature range. The removal or neutralization of the platinum (e.g. chloroplatinic acid) catalyst is desirable for long range product stability. Usually sodium bicarbonate is added to the reaction mixture to effect neutralization and the resultant slurry filtered. Of course it is preferred to use a stoichiometric excess of olefinic cyanide to insure complete reaction of all of the silicon-hydrogen bonds.

The siloxane fluids containing hydrolyzable cyanoalkyl radicals (SiOR'CN) can be prepared by the catalyzed addition of cyano substituted alkanols of the formula HOR'CN, e.g. $HOC_3H_6CN$, to the corresponding hydrosiloxanes. Said addition type process is conventional and can be promoted by a variety of catalysts such as organic derivatives of tin, platinum and other transition metals. Preferred are the organic derivatives of tin such as tin carboxylates, e.g. stannous octoate, stannous oleate, stannous laurate, dibutyl tin dilaurate and the like. The catalysts are generally used in amounts of about 0.1 to 5, usually no more than about 2, weight per cent, based on the total weight of the reactants. The reaction temperature generally ranges from about 60° to 150°C. (usually 80° to 120°C.) Of course it is preferred to use a stoichiometric excess of olefinic cyanide to insure complete reaction of all of the silicon-hydrogen bonds.

The starting materials for the above processes as well as methods for their preparation are of course all well known in the art. It is to be understood, of course, that while the siloxane fluids used in this invention can be discrete chemical compounds they are usually mixtures of various discrete siloxane species, due at least in part, to the fact that the starting materials used to produce the siloxane fluids are themselves usually mixtures. Thus it is to be also understood that the above average formula representing the siloxane fluids as used herein encompasses the presence of dihydrocarbon siloxanes as in the case of unsparged equilibrated products and the possibility of the presence of small amounts of other siloxy units, such as methyl (hydrogen) siloxy groups, in the siloxane polymers due to an incomplete reaction or the nature of the starting materials used to produce the siloxanes. Moreover the siloxane fluids employed herein need not be fractionated, as by distillation but may be sparged (i.e. stripped of lites) or unsparged.

The amount of active cyanoalkyl modified siloxane employed as the foam stabilizer may fall within the range of about 0.03 to about 2 parts by weight or greater, per hundred parts by weight of the organic polyol starting material. Preferably the siloxane fluids are employed in amounts ranging from about 0.08 to 0.6 parts by weight per 100 parts by weight of the organic polyol starting materials.

The polyhydroxyl reactants (organic polyols) employed in this invention as the starting materials to prepare the polyurethane foams can be any polyether triol containing at least 40 mole per cent of primary hydroxyl groups and having a molecular weight from about 2,000 to about 8,000. Conversely said polyether triols can contain no more than 60 mole per cent of secondary hydroxyl groups. Preferably said polyether triols contain about 60 to 90 mole per cent of primary hydroxyl groups and have a molecular weight from about 4,000 to about 7,000.

The preferred polyether triols of this invention are polyalkyleneether triols obtained by the chemical addition of alkylene oxides to trihydroxyl organic containing materials, such as glycerol; 1,2,6-hexanetriol; 1,1-trimethylolethane; 1,1,1-trimethylolpropane; 3-(2-hydroxyethoxy)-1,2-propanediol; 3-(2-hydroxypropoxy)-1, 2-propanediol; 2,4-dimethyl-2-(2 -hydroxyethoxy)methyl-pentanediol-1,5; 1,1,1--tris[(2-hydroxyethoxy)methyl]-ethane; 1,1,1-tris[(2-hydroxypropoxy)methyl]-propane; and the like, as well as mixtures thereof.

Alternatively the organic polyol starting materials of this invention can be mixtures consisting essentially of said above defined polyether triols and other polyether polyols having an average of at least two hydroxyl groups, said above defined polyether triols amounting to at least 40 preferably at least 50, weight per cent of the total polyol content of the mixtures. Illustrative of such other polyethers are triols outside of the scope defined above, diols, tetraols and polymer/polyols, and the like, as well as mixtures thereof.

Examples of such polyether polyols that can be mixed with the above defined polyether triols include those adducts of alkylene oxide to such polyols as diethylene glycol; dipropylene glycol; pentaerythritol; sorbitol; sucrose; lactose; alpha-methylglucoside; alpha-hydroxylalkylglucoside; novolac resins; water; ethylene glycol; propylene glycol, trimethylene glycol; 1,2-butylene glycol; 1,3-butanediol; 1,4-butanediol; 1,5-pentanediol; 1,2-hexane glycol; 1,10-decanediol; 1,2-cyclohexanediol; 2-butene-1,4-diol; 3-cyclohexene-1,1-dimethanol; 4-methyl-3-cyclohexene-1,1-dimethanol; 3-methylene-1,5-pentanediol; (2-hydroxyethoxy)-1-propanol; 4-(2-hydroxy-ethoxy)-1-butanol; 5-(2-hydroxypropoxy)-2-octanol; 3-allyloxy-1,5-pentanediol; 2-allyloxymethyl-2-methyl-1,3-propanediol; [4,4-pentyloxymethyl]-1,3-propane-diol; 3-(o-propenyl-phenoxy)1,2-propanediol; 2,2-diisopropylidenebis(p-phenyleneoxy)-diethanol; and the like, or phosphoric acid; benzenephosphoric acid; polyphosphoric acids such as tripolyphosphoric acid and tetrapolyphosphoric acid; and the like; as well as mixtures thereof.

Another type of polyether polyol that can be mixed with the above defined polyether triols and used as the starting materials of this invention are graft polymer/-polyether compositions obtained by polymerizing ethyleneically unsaturated monomers in a polyether as described in British Patent No. 1,063,222 and U.S. Pat. No. 3,383,351, the disclosures of which are incorporated herein by reference thereto. Suitable monomers for producing such compositions include, for example, acrylonitrile, vinyl chloride, styrene, butadiene, vinylidine chloride, and the like. Suitable polyethers for producing such compositions include, for example those polyethers hereinabove-described. These graft polymer/polyether compositions can contain from about 1 to about 70 weight per cent, preferably about 5 to about 50 weight per cent and most preferably about 10 to about 40 weight per cent of the monomer polymerized in the polyether. Such compositions are conveniently prepared by polymerizing the monomers in the selected polyether at a temperature of 40° to 150°C. in the presence of a free radical polymerization catalyst, such as peroxides, persulfates, percarbonates, perborates and azo compounds as more fully described by the above patent references. The resulting compositions may contain a small amount of unreacted polyether, monomer and free polymer as well as the graft polymer/polyether complex. Especially preferred are the graft polymer/polyethers obtained from acrylonitrile and polyether triols.

The alkylene oxides employed in producing the preferred polyethers described above normally have from 2 to 4 carbon atoms, inclusive while propylene oxide and mixtures of propylene oxide and ethylene oxide are especially preferred.

The exact organic polyol or polyols employed as the starting materials of this invention merely depend on the end use of the high resilience polyether urethane foam. For instance, the employment of polyether triols having at least 40 mole per cent primary hydroxyl groups and molecular weights from 2,000 to 8,000 preferably 4,000 to 7,000 generally have hydroxyl numbers from 84 to 21, preferably 42 to 28 and give primarily flexible polyether foams. The supplementary polyethers which may have any proportion of primary to secondary hydroxyl groups and which may be mixed with the required polyether triols can be used to control the degree of softness of the foam or vary the load bearing properties of the foam. Such limits are not intended to be restrictive, but are merely illustrative of the large number of possible combinations of polyether triols and other polyethers that can be employed.

The hydroxyl number is defined as the number of milligrams of potassium hydroxide required for the complete neutralization of the hyrolysis product of the fully acetylated derivative prepared from 1 gram of polyol or mixtures of polyols with or without other crosslinking additives used in the invention. The hydroxyl number can also be defined by the equation:

$$OH = \frac{56.1 \times 1000 \times f}{m.w.}$$

wherein

OH = hydroxyl number of the polyol.

A variety of organic isocyanates can be employed in the foam formulations of this invention for reaction with the organic polyol starting materials above described to provide high resilience polyether urethane foams. Preferred isocyanates are polyisocyanates and polyisothiocyanates of the general formula:

$(QNCY)_i$ wherein Y is oxygen or sulfur, $i$ is an integer of two or more and Q is an organic radical having the valence of $i$. For instance, Q can be a substituted or unsubstituted hydrocarbon radical, such as alkylene and arylene, having one or more aryl—NCY bonds and/or one or more alkyl—NCY bonds. Q can also include radicals such as —QZQ—, where Q is an alkylene or arylene group and Z is a divalent moiety such as —O—, —O—Q—O—, —CO—, $CO_2$, —S—, —S—Q—S—, —$SO_2$— and the like. Examples of such compounds include hexamethyl diisocyanate, 1,8-diisocyanato-p-methane, xylylene diisocyanate, $(OCNCH_2CH_2CH_2OCH_2)_2O$, 1-methyl-2,4-diisocyanatocyclohexane, phenylene diisocyanates, tolylene diisocyanates, chlorophenylene diisocyanates, diphenylmethane-4,4'-diisocyanate, naphthalene-1,5-diisocyanate, triphenylmethane-4,4'-4''-triisocyanate, and isopropylbenzene-alpha-4-diisocyanates.

Further included among the isocyanates useful in this invention are dimers and trimers of isocyanates and diisocyanates and polymeric diisocyanates such as those having the general formula:

$(QNCY)_i$ and $[Q(NCY)_i]_j$ in which $i$ and $j$ are integers of two or more, and/or (as additional components in the reaction mixtures) compounds of the general formula:

$L(NCO)_i$ in which $i$ is one or more and L is a monofunctional or polyfunctional atom or radical. Examples of this type include ethylphosphonic diisocyanate, $C_2H_5P(O)(NCO)_2$; phenylphosphonic diisocyanate, $C_6H_5P(O)(NCO)_2$; compounds containing a $\equiv$ Si—NCO group, isocyanates derived from sulfonamides ($QSO_2NCO$), cyanic acid, thiocyanic acid, and compounds containing a metal —NCO radical such as tributyltinisocyanate.

More specifically, the polyisocyanate component employed in the polyurethane foams of this invention also includes the following specific compounds as well as mixtures of two or more of them: 2,4-tolylene diisocyanate, 2,6-tolylene diisocyanate, crude tolylene diisocyanate, bis(4-isocyanatophenyl)methane, polymethylene polyphenylisocyanates that are produced by phosgenation of anilineformaldehyde condensation products, dianisidine diisocyanate, toluidine diisocyanate, xylylene diisocyanate, bis(2-isocyanatoethyl)-fumarate, bis(2-isocyanatoethyl) carbonate, 1,6-hexamethylene-diisocyanate, 1,4-tetramethylene-diisocyanate, 1,10-deca-methylene-diisocyanate, cumene-2,4-diisocyanate, 4-methoxy-1,3-phenylene-diisocyanate 4-chloro-1,3-phenylenediisocyanate, 4-bromo-1,3-phenylene-diisocyanate, 4-ethoxy-1,3-phenylene-diisocyanate, 2,4'-diisocyanato-diphenylether, 5,6-dimethyl-1,3-phenylene-diisocyanate, 2,4-dimethyl-1,3-phenylenediisocyanate, 4,4'-diisocyanatodiphenylether, bis 5,6-(2-iso-cyanato-ethyl)bicyclo[2,2,1]hept-2-ene, benzidinediisocyanate, 4.6-dimethyl-1,3-phenylenediisocyanate, 9,10-anthracenediisocyanate, 4,4'-diisocyanatodibenzyl, 3,3-dimethyl-4,4'-diisocyanatodiphenylmethane, 2,6-dimethyl-4,4'-diisocyanatodiphenyl, 2,4-diisocyanatostilbene, 3,3'-dimethyl-4,4'-diisocyanatodiphenyl, 3,3'-dimethoxy-4,4'-diisocyanatodiphenyl, 1,4-anthracenediisocyanate, 2,5-fluorenediisocyanate, 1,8-naphthalenediisocyanate, 2,6-diisocyanatobenzfuran, 2,4,6-toluenetriisocyanate, and many other organic polyisocyanates that are known in the art, such as those that are disclosed in an article by Siefken, Ann., 565, 75 (1949). In general, the aromatic polyisocyanates are preferred.

Particularly useful isocyanate components of high resilience cold cure formulations within the scope of this invention are combinations of isomeric tolylene diisocyanates and polymeric isocyanates having units of the formula

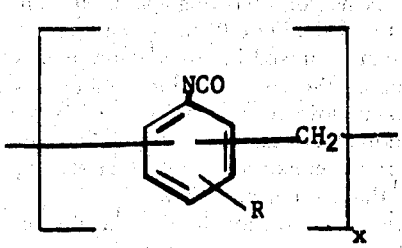

wherein R is hyrogen and/or lower alkyl and $x$ has a value of at least 2.1. Preferably the lower alkyl radical is methyl and $x$ has a value of from 2.1 to about 3.0.

The amount of polyisocyanate employed will vary slightly depending on the nature of the polyurethane being prepared. In general the polyisocyanates are employed in the foam formulations of this invention in amounts that provide from 80 to 150 per cent, preferably from 90 to 110 per cent of the stoichiometric amount of the isocyanato groups required to react with all of the hydroxyl groups of the organic polyol starting materials and with any water present as a blowing agent. Most preferably, a slight amount of isocyanato groups in excess to the stiochiometric amount is employed.

The blowing agents employed in this invention include methylene chloride, water, liquefied gases which have boiling points below 80°F. and above −60°F., or by other inert gases such as nitrogen, carbon dioxide, methane, helium and argon. Suitable liquefied gases include saturated aliphatic fluorohydrocarbons which vaporize at or below the temperature of the foaming mass. Such gases are at least partially fluorinated and can also be otherwise halogenated. Fluorocarbon blowing agents suitable for use in foaming the formulations of this invention include trichloromonofluoromethane, dichlorodifluoromethane, dichlorofluoromethane, 1,1-chloro-1-fluoroethane, 1-chloro-1,1-difluoro, 2,2-dichloroethane, and 1,1,1-trifluoro, 2-chloro-2-fluoro, 3,3-difluoro-4,4,4-trifluorobutane. The amount of blowing agent used will vary with density desired in the foamed product. Usually from 2 to 20 parts by weight of the blowing agent per 100 parts by weight of the organic polyol starting materials are preferred.

The catalysts employed in this invention include any of the catalyst used in producing conventional flexible polyurethane foam. Illustrative catalysts are conventional amine catalysts such as N-methyl morpholine, N-ethyl morpholne, hexadecyl dimethylamine, triethylamine, N,N,N',N'-tetramethyl-1,3-butanediamine, N,N-dimethylethanol-amine, bis(2-dimethyaminoethyl)ether, N,N,N',N'-tetramethyl ethylenediamine, 4,4'-methylene bis(2-chloroaniline), dimethyl benzylamine, N-coco morpholine, triethylene diamine, [1,4-diazobicyclo (2,2,2)-octane ], the formate salts or triethylene diamine, other salts of triethylene diamine and oxyalkylene adducts of primary and secondary amino groups, and the like. If desired, conventional organo metal catalysts may be used to supplement the amine catalysts. Illustrative of such metal catalysts are the tin salts of various caboxylic acids e.g. stannous octoate, dibutyl tin dilaurate, nickel acetylacetonates, and the like. Generally the total amount of catalyst employed in the mixtures will range from 0.1 to 2 weight per cent based on the total weight of the organic polyol starting materials.

The relative amounts of the various components reacted in accordance with the above described process for producing high resilience polyether urethane foams in accordance with this invention are not narrowly critical. The polyether and the polyisocyanate are present in the foam formulations used to produce such foams, i.e. a major amount. The relative amounts of these two components is the amount required to produce the urethane structure of the foam and such relative amounts are well known in the art. The blowing agent, catalyst and siloxanes are each present in a minor amount necessary to achieve the function of the component. Thus, the blowing agent is present in a minor amount sufficient to foam the reaction mixture, the catalyst is present in a catalytic amount (i.e., an amount sufficient to catalyze the reaction to produce the urethane at a reasonable rate) and the siloxane fluids are present in a foam-stabilizing amount (i.e., in an amount sufficient to stabilize the foam against voids and shrinkage). Preferred amounts of these various components are given hereinabove The high resilience cold cure urethane foams produced in accordance with this invention can be used for the same purposes as corresponding conventional hot cure polyether urethane foams, e.g. they can be used where ever cushioning is desired, e.g. in furniture; in transportation systems, automobiles, planes, etc.; in carpeting; in the packaging of delicate objects; and the like.

Other additional ingredients can be employed in minor amounts in producing the high resilience polyether urethane foams in accordance with the process of this invention, if desired, for specific purposes. Thus inhibitors (e.g. d-tartaric acid and tetiary-butyl pyrocatechol, "Ionol") can be employed to reduce any tendency of the foam to hydrolytic or oxidative instability. Flame retardants (e.g. tris(2-chloroethyl)phosphate) can be used. Dihydrocarbon silicone oils, e.g. dimethylsiloxanes, the siloxane-oxyalkylene block copolymers described in U.S. Patent application Ser. No. 84,181 filed Oct. 26, 1970, now U.S. Pat. No. 3,741,917 and the aralkyl modified siloxanes described in U.S. Patent application Ser. No. 305,713 filed Nov. 13, 1972, now U.S. Pat. No. 3,839,384 may be mixed if desired with the siloxanes employed in this invention. While such mixtures are not required they may help expand the usefulness of the siloxane fluids employed herein by increasing the adaptability of the siloxane fluid to a variety of foam formulations. Of course any organic solvent for the amine catalysts, e.g. polyols such as hexylene glycol (i.e. 2-methyl-2,4-pentanediol), dipropylene glycol, and the like can be used which substantially do not adversely effect the operation of the process or reactants. Examples of other additives that can be employed are crosslinkers such as glycerol, triethanol amine, and their oxyalkylene adducts, and anti-yellowing agents.

An additional feature of the instant invention are the novel compositions suitable for use in producing the high resilience polyether urethane foam. For example it may be desirable, particularly on a commercial scale to employ the cyanoalkyl modified siloxane fluid in a diluted form, i.e. in the form of a siloxane fluid-solvent solution premix or a siloxane fluid-solvent-catalyst solution premix. Such solution premixtures can help serve to eliminate any mixing, metering, or settling problems. Moreover, fewer streams of ingredients may be needed at the mixing head of the operational apparatus. Of considerable importance is that the formulator has the latitude to select the particular solent which best suits the system and minimize or eliminate any loss of foam properties. Siloxane fluid-solvent-catalyst premixes can also be used since the selected solent can be one which serves the dual role of solvent for the catalysts as well as the siloxane fluid. This option of formulating a premix simplifies the foaming operation and improves the precision of metering ingredients. While any suitable organic solvent such as hydrocarbon, halohydrocarbons, organic hydroxyl compounds, alkyl phthalates, and the like may be employed, preferably when employed the solvent selected should be one in which the cyanoalkyl modified siloxane fluid is substantially soluble. For example, it is preferred that at least five parts by weight of the cyanoalkyl modified siloxane oil be soluble in 95 parts by weight of solvent. More preferably the minimum percentage of cyanoalkyl modified siloxane fluid in the siloxane fluid-solvent or siloxane fluid-solvent-catalyst solutions should be in the range of at least about ten to at least about 30 weight percent. Of course it is understood that such solvents need not be employed and that the maximum percentage of cyanoalkyl modified siloxane fluid in said solvent solutions is not critical. Moreover, when employed such solvent solutions should of course be correlated to the amounts of active cyanoalkyl modified siloxane fluid that may be employed per hundred parts by weight of the organic polyol starting material as outlined above. The same correlation should also be made with regard to catalyst when a siloxane fluid-solvent-catalyst solution is employed. Preferably the solvent for the cyanoalkyl modified siloxane fluid is an organic hydroxyl compound such as hydroxyl terminated organic ether compounds. More preferably they are polyether triols, diols, and mono-ols such as the adducts of ethylene oxide, propylene oxide, butylene oxide, with starters such as glycerol, water, trimethylolpropane, 1,2,6-hexanetriol, ethylene glycol, butanol, nonylphenol, and the like. Of course the oxyalkylene units of such adducts may be of different types, e.g. oxypropylene and oxyethylene groups, and may be randomly distributed or in blocks. The most preferred solvents are the polyether triols having all or predominantly oxypropylene units in the oxyalkylene portion and having molecular weights in the range from about 2,000 to 6,000 inasmuch as they may be the same, as or similar to the primary triols employed as the organic polyol starting material of the foam formulation. Moreover this discovery concerning the solubility of the cyanoalkyl modified siloxane fluids of this invention can be regulated and controlled. For stability reasons it is preferred to use the siloxane fluids containing non-hydrolyzable cyanoalkyl radicals (Si—R'CN) in said solvent solutions.

In accordance with this invention, the cold cure polyether urethane foams can be produced by any suitable technique. The preferred process is a one-step or one shot technique wherein all of the reactants are reacted simultaneously with the foaming operation. A second general process is called the prepolymer process whereby a prepolymer is formed by reacting the polyether starting material with a small excess of the isocyanate and later foaming the prepolymer by the reaction with water or an inert blowing agent. Another method which can be used is the quasi-prepolymer technique which involves reacting a large excess of the isocyanate with the polyether starting material and then subsequently foaming this product with additional polyether in the presence of a blowing agent. Of course it is understood that the ingredients of the foam forming formation can be mixed in any suitable manner prior to commencing the cure reaction. Sometimes it is preferred to employ various premixes such as a premixture of the polyether starting material and siloxane fluid stabilizer; a premixture of polyether starting material, siloxane fluid, water and catalyst; a premixture of the polyisocyanate and siloxane fluid, a siloxane fluid-solvent-catalyst solution as outlined above; and the like. Because of the high exothermic nature of the reaction high resilience urethane foams are rapidly produced without the need of any external heat by mixing the reactants at ambient temperatures and pouring the foaming reaction mixture into a suitable mold and allowing the foam to cure itself. Of course, if desired the overall reaction can be even further accelerated by preheating the mold and/or employing conventional high temperature post curing procedures. Within a shorter period of time the cold cure process, with or without post cure, simultaneously achieves a greater degree of cure throughout the entire foam, and shorter tack free and demolding time, then is generally achieved with conventional hot cure processes. For instance, cold cure foams can be removed from the mold far sooner without substantial damage to the surface than conventional hot cure foams. Of course it is to be undestood that the high resilience polyether urethane foam of this invention can also be prepared in slabstock form, if desired.

The following examples illustrate the present invention and are not to be regarded as limitative. It is to be understood that the average formulas of the siloxane fluid products are based on the mole ratios of the starting materials employed, "Me" represents a methyl radical, "Conc." represents concentration, "p.h.p." refers to parts of siloxane-solvent solution per hundred parts of organic polyol starting material unless otherwise designated, "100 Index" indicates that the number of moles of NCO groups is equal to the total moles of hydroxyl groups in the foam formulation, one drop of tetramethylammonium silanolate is equivalent to 4.57 ppm as K, and that all of the parts, precentages and proportions referred to herein and in the appended claims are by weight unless otherwise indicated.

EXAMPLE 1

Into a flask equipped with a thermometer, mechanical stirrer, condenser and nitrogen blow-by were charged about 13.5 grams of hexamethyldisiloxane, about 42.5 grams of a cyclic gamma-cyanopropylmethylsiloxane having a viscosity of about 617 centistokes at 25°C., about 19 grams of cyclic dimethylsiloxane tetramer,, and about 21 drops of tetramethyl ammonium silanolate catalyst (128 ppm as K). The mixture was then equilibrated with stirring under a nitrogen blanket for 2 hours at 90°C., followed by an additional 1 ½ hours at 150°C. to deactivate the catalyst, then cooled and filtered. There was obtained a clear cyanoalkyl-modified siloxane fluid product having the average formula

$Me_3SiO(Me_2SiO)_{3.1}[NC(CH_2)_3SiMeO]_{4.0}SiMe_3$.

Said siloxane has an average molecular weight of about 898, a viscosity of about 47.9 centistokes at 25°C., a siloxane content of about 69.7 wt. %, and is hereinafter referred to as Siloxane I.

EXAMPLE 2

Example 1 was repeated except about 14.2 grams of hexamethyldisiloxane, about 38.3 grams of the cyclic gamma-cyanopropyl-methylsiloxane and about 22.5 grams of cyclic dimethylsiloxane tetramer were used and the reaction maintained at 90°C. for 1½ hours followed by an additional 1½ hour at 150°C. There was obtained a clear cyanoalkyl-modified siloxane fluid having the average formula

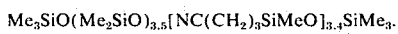
Me$_3$SiO(Me$_2$SiO)$_{3.5}$[NC(CH$_2$)$_3$SiMeO]$_{3.4}$SiMe$_3$.

Said siloxane has an average molecular weight of about 857, a viscosity of about 36.9 centistokes at 25°C., a siloxane content of about 72.7 wt. %, and is hereinafter referred to as Siloxane II.

EXAMPLE 3

Example 1 was repeated except about 14.7 grams of hexamethyldisiloxane, about 34.8 grams of the cyclic gamma-cyanopropyl-methylsiloxane, about 25.5 grams of cyclic dimethylsiloxane tetramer, and about 7 drops of the tetramethyl ammonium silanolate catalyst (43 ppm as K) were used. The reaction was maintained at 90°C. for 2 hours followed by an additional 1½ hour at 150°C. There was obtained a clear cyanoalkyl-modifed siloxane fluid having the average formula

Me$_3$SiO(Me$_2$SiO)$_{3.3}$[NC(CH$_2$)$_3$SiMeO]$_{3.0}$SiMe$_3$.

Said siloxane has an average molecular weight of about 827, a viscosity of about 31.4 centistokes at 25°C., a siloxane content of about 75.1 wt. %, and is hereinafter referred to as Siloxane III.

EXAMPLE 4

Example 1 was repeated using about 17.4 grams of hexamethyldisiloxane, about 34.3 grams of the cyclic gamma-cyanopropyl-methylsiloxane and about 23.3 grams of cyclic dimethylsiloxane tetramer and the reaction maintained at 90°C. for 2½ hours followed by an additional 3 hours at 150°C. There was obtained a clear cyanoalkyl-modified siloxane fluid having the average formula

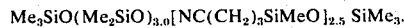
Me$_3$SiO(Me$_2$SiO)$_{3.0}$[NC(CH$_2$)$_3$SiMeO]$_{2.5}$SiMe$_3$.

Said siloxane has an average molecular weight of about 700, a viscosity of about 22.4 centistokes at 25°C., a siloxane content of about 75.5 wt. %, and is hereinafter referred to as Siloxane IV.

EXAMPLE 5

Example 1 was repeated except about 18.3 grams of hexamethyldisiloxane, about 35.8 grams of the cyclic gamma-cyanopropyl-methylsiloxane and about 20.9 grams of cyclic dimethylsiloxane tetramer were used and the reaction maintained at 90°C. for 1½ hours followed by an additional 1 ¼ hour at 150°C. There was obtained a clear cyanoalkyl-modified siloxane fluid having the average formula

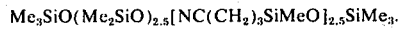
Me$_3$SiO(Me$_2$SiO)$_{2.5}$[NC(CH$_2$)$_3$SiMeO]$_{2.5}$SiMe$_3$.

Said siloxane has an average molecular weight of about 665, a viscosity of about 21.6 centistokes at 25°C., a siloxane content of about 74.4 wt. %, and is hereinafter referred to as Siloxane V.

EXAMPLE 6

Example 1 was repeated except about 21.9 grams of hexamethyldisiloxane, about 30.1 grams of the cyclic gamma-cyanopropyl-methylsiloxane, about 23 grams of cyclic dimethylsiloxane tetramer, and about 14 drops of the tetramethyl ammonium silanolate catalyst (85 ppm as K) were used. The reaction was maintained at 90°C. for 1½ hours followed by an additional 1¼ hour at 150°C. There was obtained a clear cyanoalkyl-modified siloxane fluid having the average formula

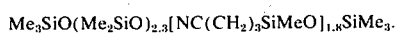
Me$_3$SiO(Me$_2$SiO)$_{2.3}$[NC(CH$_2$)$_3$SiMeO]$_{1.8}$SiMe$_3$.

Said siloxane has an average molecular weight of about 554, a viscosity of about 12.8 centistokes at 25°C., a siloxane content of about 78.5 wt. %, and is hereinafter referred to as Siloxane VI.

EXAMPLE 7

Example 5 was repeated except about 22.7 grams of hexamethyldisiloxane, about 26.5 grams of the cyclic gamma-cyanopropyl-methylsiloxane and about 25.8 grams of cyclic dimethylsiloxane tetramer were used. There was obtained a clear cyanoalkyl-modified siloxane fluid having the average formula

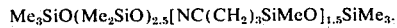
Me$_3$SiO(Me$_2$SiO)$_{2.5}$[NC(CH$_2$)$_3$SiMeO]$_{1.5}$SiMe$_3$.

Said siloxane has an average molecular weight of about 538, a viscosity of about 9.8 centistokes at 25°C., a siloxane content of about 81 wt. %, and is hereinafter referred to as Siloxane VII.

EXAMPLE 8

Example 5 was repeated except about 27.8 grams of hexamethyldisiloxane, about 21.8 grams of the cyclic gamma-cyanopropyl-methylsiloxane and about 25.4 grams of cyclic dimethylsiloxane tetramer were used. There was obtained a clear cyanoalkyl-modified siloxane fluid having the average formula

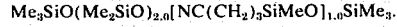
Me$_3$SiO(Me$_2$SiO)$_{2.0}$[NC(CH$_2$)$_3$SiMeO]$_{1.0}$SiMe$_3$.

Said siloxane has an average molecular weight of about 437, a viscosity of about 6.4 centistokes at 25°C., a siloxane content of about 84.4 wt. %, and is hereinafter referred to as Siloxane VIII.

EXAMPLE 9

Example 1 was repeated except about 162 grams of hexamethyldisiloxane, about 205 grams of the cyclic gamma-cyanopropyl-methylsiloxane, about 178 grams of the cyclic dimethylsiloxane tetramer, and about 140 drops of the tetramethyl ammonium silanolate catalyst (117 ppm as K) were used. The reaction was maintained at 90°–95°C. for 4 hours followed by heating at 150°C. for an additional 2 hours. Upon cooling and filtering there was obtained a clear cyanoalkyl-modified siloxane fluid having the average formula

Me$_3$SiO(Me$_2$SiO)$_{2.4}$[NC(CH$_2$)$_3$SiMeO]$_{1.6}$SiMe$_3$.

Said siloxane has an average molecular weight of about 545, a viscosity of about 9.9 centistokes at 25°C., a siloxane content of about 80 wt. %, and is hereinafter referred to as Siloxane IX.

EXAMPLE 10

Example 1 was repeated except about 11.8 grams of hexamethyldisiloxane, about 55.7 grams of the cyclic gamma-cyanopropyl-methylsiloxane, about 32.5 grams of the cyclic dimethylsiloxane tetramer, and about 28 drops of the tetramethyl ammonium silanolate catalyst (128 ppm as K) were used. The reaction was maintained at 90°–95°C. for 4 hours followed by heating at 150°C. for an additional 2 hours. Upon cooling and filtering there was obtained a clear cyanoalkyl-modified siloxane fluid having the average formula

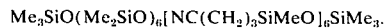

$Me_3SiO(Me_2SiO)_6[NC(CH_2)_3SiMeO]_6SiMe_3$.

Said siloxane has an average molecular weight of about 1368, a viscosity of about 99.4 centistokes at 25°C., a siloxane content of about 70.6, and is hereinafter referred to as Siloxane X.

EXAMPLE 11

Into a 250 ml. three-necked flask equipped with a thermometer, mechanical stirrer, condenser and nitrogen blow-by were charged about 16.2 grams (0.1 mole) of hexamethyldisiloxane ($Me_3SiOSiMe_3$), about 29.6 grams (0.4 mole) of cyclic dimethylsiloxane tetramer $[(Me_2SiO)_4]$, and about 35.6 grams (0.28 mole) of a cyclic gamma-cyanopropyl-methylsiloxane $[NC(CH_2)_3SiMeO]$ having a viscosity of about 2100 centistokes at 25°C. The mixture was then equilibrated under a nitrogen blanket by stirring it vigorously at room temperature while 0.75 weight percent (0.61 grams) of trifluoromethane sulfonic acid catalyst was added to the system. Agitation was maintained for 16 hours. At this time an additional 0.025 weight percent of more trifluoromethane sulfonic acid was added and the mixture became homogeneous within 2 hours. Equilibration was continued for 4 more hours at room temperature. The equilibrated product was neutralized with about 10 grams of sodium bicarbonate and filtered. There was obtained a clear cyanoalkyl-modified siloxane fluid product having the average formula

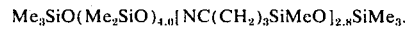

$Me_3SiO(Me_2SiO)_{4.0}[NC(CH_2)_3SiMeO]_{2.8}SiMe_3$.

Said siloxane has an average molecular weight of about 814, a viscosity of about 35.8 centistokes at 25°C., a siloxane content of about 76.6 wt. %, and is hereinafter referred to as Siloxane XI.

EXAMPLE 12

Example 11 was repeated except about 65 grams of hexamethyldisiloxane, about 89 grams of cyclic dimethylsiloxane tetramer, about 76 grams of the cyclic gamma-cyanopropyl-methylsiloxane were used along with increments of about 1.15 grams and 0.575 grams of the trifluoromethane sulfonic acid catalyst and about 30 grams of sodium bicarbonate to neutralize the equilibrated product. There was obtained a clear cyanoalkyl-modified siloxane fluid product having the average formula

$Me_3SiO(Me_2SiO)_3[NC(CH_2)_3SiMeO]_{1.5}SiMe_3$.

Said siloxane has an average molecular weight of about 575, a viscosity of about 17.0 centistokes at 25°C., a siloxane content of about 82 wt. %, and is hereinafter referred to as Siloxane XII.

EXAMPLE 13

Example 6 was repeated except about 33.5 grams of hexamethyldisiloxane, about 26.2 grams of the cyclic gamma-cyanopropyl-methylsiloxane and about 15.3 grams of cyclic dimethylsiloxane tetramer were used. There was obtained a clear cyanoalkyl-modified siloxane fluid having the average formula

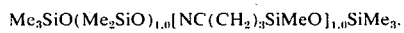

$Me_3SiO(Me_2SiO)_{1.0}[NC(CH_2)_3SiMeO]_{1.0}SiMe_3$.

Said siloxane has an average molecular weight of about 363, a viscosity of about 5 centistokes at 25°C., a siloxane content of about 81.3 wt. %, and is hereinafter referred to as Siloxane XIII.

EXAMPLE 14

Example 6 was repeated except about 4.8 grams of hexamethyldisiloxane, about 37.5 grams of the cyclic gamma-cyanopropyl-methylsiloxane and about 32.7 grams of cyclic dimethylsiloxane tetramer were used. There was obtained a clear cyanoalkyl-modified siloxane fluid having the average formula

$Me_3SiO(Me_2SiO)_{15}[NC(CH_2)_3SiMeO]_{10}SiMe_3$.

Said siloxane has an average molecular weight of about 2542, a viscosity of about 166 centistokes at 25°C., a siloxane content of about 73.2 wt. %, and is hereinafter referred to as Siloxane XIV.

EXAMPLE 15

Example 1 was repeated except about 5.6 grams of hexamethyldisiloxane, about 43.9 grams of the cyclic gamma-cyanopropyl-methylsiloxane and about 25.5 grams of cyclic dimethylsiloxane tetramer were used and the reaction maintained at 90°C. for 2½ hours, at 100°C. for one-half hour, at 110°C. for one-half hour followed by an additional hour at 150°C. There was obtained a clear cyanoalkyl-modified siloxane fluid having the average formula

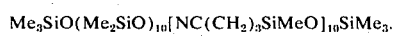

$Me_3SiO(Me_2SiO)_{10}[NC(CH_2)_3SiMeO]_{10}SiMe_3$.

Said siloxane has an average molecular weight of about 2172, a viscosity of about 220 centistokes at 25°C., a siloxane content of about 68.7 wt. %, and is hereinafter referred to as Siloxane XV.

EXAMPLE 16

Into a flask equipped with a thermometer, mechanical stirrer, condenser and nitrogen blow-by were charged about 162 grams of hexamethyldisiloxane, about 95.8 grams of a cyclic gamma-cyanopropylmethylsiloxane having a viscosity of about 617 centistokes at 25°C., about 178.3 grams of cyclic dimethylsiloxane tetramer, and about 2 weight per cent of concentrated $H_2SO_4$ catalyst. The mixture was then equilibrated with stirring under a nitrogen blanket for about 4 hours at 40°–45°C., then neutralized with sodium bicarbonate and filtered. There was obtained a clear cyanoalkyl-modified siloxane fluid product having the average formula

$Me_3SiO(Me_2SiO)_{2.41}[NC(CH_2)_3SiMeO]_{0.75}SiMe_3$.

Said siloxane has an average molecular weight of about 436, a viscosity of about 4.6 centistokes at 25°C., a siloxane content of about 88.2 wt. %, and is hereinafter referred to as Siloxane XVI and represents a siloxane of this invention.

EXAMPLE 17

Into a flask equipped with a thermometer, mechanical stirrer, condenser and nitrogen blow-by were charged about 162 grams of hexamethyldisiloxane, about 82.6 grams of a cyclic gamma-cyanopropylmethylsiloxane having a viscosity of about 617 centistokes at 25°C., about 195.4 grams of cyclic dimethylsiloxane tetramer, and about 2 weight percent of concentrated $H_2SO_4$ catalyst. The mixture was then equilibrated with stirring under a nitrogen blanket for about 4 hours at 40°–45°C., then neutralized with sodium bicarbonate and filtered. There was obtained a clear cyanoalkyl-modified siloxane fluid product having the average formula

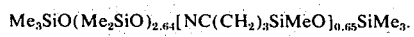

$Me_3SiO(Me_2SiO)_{2.6}[NC(CH_2)_3SiMeO]_{0.65}SiMe_3$.

Said siloxane has an average molecular weight of about 440, a viscosity of about 4.6 centistokes at 25°C., a siloxane content of about 90 wt. %, and is hereinafter referred to as Siloxane XVII and represents a siloxane of this invention.

EXAMPLE 18

Into a flask equipped with a thermometer, mechanical stirrer, condenser and nitrogen blow-by were charged about 162 grams of hexamethyldisiloxane, about 108 grams of a cyclic gamma-cyanopropylmethylsiloxane having a viscosity of about 617 centistokes at 25°C., about 222 grams of cyclic dimethylsiloxane tetramer, and about 2 weight per cent of concentrated $H_2SO_4$ (10 grams) catalyst. The mixture was then equilibrated with stirring under a nitrogen blanket for about 4 hours at 40°–45°C., then neutralized with sodium bicarbonate and filtered. There was obtained a clear cyanoalkyl-modified siloxane fluid product having the average formula

$Me_3SiO(Me_2SiO)_{3.0}[NC(CH_2)_3SiMeO]_{0.85}SiMe_3$.

Said siloxane has an average molecular weight of about 490, a viscosity of about 5.3 centistokes at 25°C. and is hereinafter referred to as Siloxane XVIII and represents a siloxane of this invention.

EXAMPLE 19

Example 18 was repeated except about 13.5 grams of the hexamethyldisiloxane, about 42.5 grams of the cyclic gamma-cyanopropylmethylsiloxane, and 178 grams of the cyclic dimethylsiloxane tetramer were used. There was obtained a clear cyanoalkyl-modified siloxane fluid product having the average formula

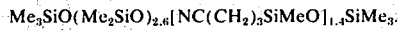

$Me_3SiO(Me_2SiO)_{2.6}[NC(CH_2)_3SiMeO]_{1.4}SiMe_3$.

having an average molecular weight of about 530 and is hereinafter referred to as Siloxane XIX and represents a siloxane of this invention.

For the sake of brevity the above designations given for the siloxane fluids along with the following designations are used to denote the various ingredients employed in the following examples.

TABLE 1

| Designation Organic Polyols | Composition |
|---|---|
| E1 | This is a polyether triol, mol. wt. about 6,000; hydroxyl No. about 27; containing about 85 mole % primary hydroxyl groups produced by reacting about 89% propylene oxide and about 11% ethylene oxide with glycerol. |
| E2 | This is a polyether triol, mol. wt. about 5,000; hydroxyl No. about 34; containing about 75 mole % primary hydroxyl groups produced by reacting about 84% propylene oxide and about 16% ethylene oxide with glycerol. |
| E3 | This is a graft polymer/polyol; about 80 wt.% polyol, 10 wt.% styrene and 10 wt.% acrylonitrile; having a hydroxyl No. of about 28, produced by polymerizing styrene and acrylonitrile in E2. |
| Polyisocyanates | Composition |
| C1 | This is a mixture of about 80 wt.% 2,4-tolylene diisocyanate and about 20 wt.% 2,6-toluene diisocyanate. |
| C2 | This is a polymethylene polyphenyl isocyanate polymer containing about 2.6–2.9 moles of NCO per mole of polymer and having an isocyanate content of about 31.4 per cent. |
| C3 | This is a composition of about 80 wt.% C1 and about 20 wt.% C2. |
| Catalyst | Composition |
| A1 | This is a composition consisting of about 70 wt.% bis(N,N-dimethylaminoethyl) ether and about 30 wt.% dipropylene glycol solvent. |
| Siloxane Solvents | Composition |
| S1 | This is a polyether triol, mol. wt. about 3000 produced by reacting propylene oxide with glycerol, and a hydroxyl number of about 56. |

EXAMPLE 20

The foam formulations employed in producing the foams in this example were identical save for variations in the amount of cyanoalkyl modified siloxane fluid employed. The high resilience polyether urethane foams were all prepared and evaluated in the following manner.

A blend of polyether triols E2 and E3 was dispersed into a paper cup at about 20° to 30°C. Then the siloxane fluid and dibutyltin-dilaurate catalyst were added via a 5 cc syringe and dispersed with a spatula followed by a premix of water, A1 catalyst, solid triethylenediamine and N-ethylmorpholine catalyst which was also dispersed in the mixture without using a baffle. The mixture was then placed under a drill press mixer and agitated for about 10 seconds at 2150 rmp, while the cup was turned around to insure proper mixing. Without stopping the drill press polyisocyanate C3 was rapidly added and mixed for about 7 seconds. The foam forming mixture was then rapidly poured into an 8 × 8 × 6 inches parchment lined cake box which was supported by a wooden mold and allowed to cure. The high resilience polyether urethane foam product was allowed to rest for at least two minutes after completion of the foam rise to avoid densification at the bottom of the foam bun. Thereafter the foam while still in the cake box was placed in an oven at 125°C. for about 10 minutes to reduce tackiness and facilitate separation of the paper liner from the mold and cutting of the foam samples. The foam was allowed to stand for about 1 hour before cutting when it was then sliced 1½ inches from the bottom with a band saw.

Said foam formulations all contained 100 parts by weight of the polyether blend on the order of about 60 parts (150 grams) of polyether triol E2 and 40 parts (100 grams) of polyether triol E3; about 2.6 parts by weight (6.5 grams) of water; about 0.1 parts by weight (0.25 grams) of amine catalyst A1; about 1.2 parts by weight (3.0 grams) of N-ethylmorpholine catalyst; about 0.12 parts by weight (0.3 grams) of solid triethylene diamine catalyst; about 0.015 parts by weight (0.038 grams) of dibutyltindilaurate catalyst and about 33.9 parts by weight (84.8 grams) of polyisocyanate C3 (100 Index). The cyanoalkyl modified siloxane fluid was used in the form of a siloxane fluid-solvent solution composed of about 22 parts by weight of siloxane fluid and 78 parts by weight of solvent S1 unless otherwise noted. The amount and particular siloxane fluid employed was varied and the recorded properties of the various foam samples are given in TABLE 2 below.

The breathability measurements, except for Foam Nos. 28 and 29 were all recorded by a Gurley Densometer which measures the porosity or air resistance of the foam as shown by the time in seconds for a given volume of air (300 cc's of air) to pass through 1 square inch of foam. The value recorded is the average value of five such measurements given in seconds per 300 cc's of displaced air. The breathability measurements of Foam Nos. 28 and 29 denote the porosity of the foam and is roughly proportioned to the number of open cells in the foam. They were measured by taking a 2 × 2 × 1 inches piece of foam cut from near the center of the bun using a Nopco Foam Breathability Tester, GP-2 Model 40 GD 10. Air is drawn through the 1 inch portion at a pressure differential of 0.5 inches of water less than atmospheric pressure. The air flow is parallel to the direction of original foam rise. The degree of openness of the foam (or foam breathability) is measured by air flow and is designated in standard cubic feet per minute.

TABLE 2

| Foam No. | Siloxane Fluid No. | Siloxane Solution Conc. (php) | Foam Breathability | Cells/Inch | Shrinkage | Cell Uniformity |
|---|---|---|---|---|---|---|
| A | Control | None | 4.7 | 16 | None | Severe Voids - Irregular |
| 1 | I | 0.3 | 6.5 | 22 | None | Severe Voids - Irregular |
| 2 | I | 0.75 | 6.1 | 24 | None | Moderate Voids - Irregular |
| 3 | I | 1.12 | 8.5 | 24 | None | No Voids - Uniform |
| 4 | II | 0.3 | 6.2 | 22 | None | Slight Voids - Irregular |
| 5 | II | 0.75 | 7.5 | 24 | None | No Voids - Uniform |
| 6 | II | 1.12 | 13.2 | 26 | None | No Voids - Uniform |
| 7 | III | 0.3 | 7.8 | 24 | None | No Voids - Uniform |
| 8 | III | 0.75 | 11.2 | 22 | None | No Voids - Uniform |
| 9 | III | 1.12 | 18.8 | 28 | None | No Voids - Uniform |
| 10 | IV | 0.3 | 8.5 | 24 | None | Slight Voids - Irregular |
| 11 | IV | 0.75 | 8.7 | 26 | None | No Voids - Uniform |
| 12 | IV | 1.12 | 10.7 | 28 | None | No Voids - Uniform |
| 13 | V | 0.3 | 9.0 | 24 | None | Severe Voids - Irregular |
| 14 | V | 0.75 | 9.1 | 26 | None | No Voids - Uniform |
| 15 | V | 1.12 | 7.9 | 26 | None | No Voids - Uniform |
| 16 | VI | 0.3 | 8.5 | 24 | None | Moderate Voids - Irregular |
| 17 | VI | 0.75 | 7.3 | 24 | None | No Voids - Uniform |
| 18 | VI | 1.12 | 9.5 | 24 | None | No Voids - Uniform |
| 19 | VII | 0.3 | 7.6 | 24 | None | Slight Voids - Irregular |
| 20 | VII | 0.75 | 8.6 | 26 | None | No Voids - Uniform |
| 21 | VII | 1.12 | 11.0 | 28 | None | No Voids - Uniform |
| 22 | VIII | 0.3 | 7.6 | 22 | None | Slight Voids - Irregular |
| 23 | VIII | 0.75 | 9.3 | 24 | None | No Voids - Uniform |
| 24 | VIII | 1.12 | 9.4 | 24 | None | No Voids - Uniform |
| 25 | IX | 1.12 | 7.1 | 26 | None | No Voids - Uniform |
| 26 | X | 0.375 | 6.9 | 24 | None | No Voids - Uniform |
| 27 | X | 0.75 | 15.4 | 26 | None | Slight Voids - Irregular |
| 28 | XI | 0.1+ | 0.75 | 32 | None | No Voids - Uniform |
| 29 | XII | 0.1+ | 1.05 | 34 | None | No Voids - Uniform |
| Siloxanes Not of This Invention | | | | | | |
| 30 | XIII | 1.12 | 7.4 | 20 | None | Severe Voids - Irregular |
| 31 | XIII | 2.25 | 7.6 | 22 | None | Severe Voids - Irregular |
| 32 | XIV | 0.3 | — | — | Severe | No Voids - Uniform |
| 33 | XIV | 0.75 | — | — | Severe | No Voids - Uniform |
| 34 | XV | 0.3 | — | — | Severe | No Voids - Uniform |
| 35 | XV | 0.75 | — | — | Severe | No Voids - Uniform |

+Evaluated as 100 per cent active siloxane fluid (not solvent).

EXAMPLE 21

Another series of high resilience polyether urethane foam was produced in the same manner as Example 20 except that the foam formulations all contained 100 parts by weight of the polyether blend on the order of about 50 parts (100 grams) of polyether triol E1 and about 50 parts (100 grams) of polyether triol E3; about 2.7 parts (5.4 grams) of water; about 0.08 parts (0.16 grams) of amine catalyst A1; about 0.8 parts of N-ethylmorpholine catalyst; about 0.15 parts (0.30 grams) of solid triethylenediamine catalyst; about 0.033 parts (0.066 grams) of dibutyltindilaurate catalyst, about 5.7 parts (11.4 grams) of trichlorofluoromethane blowing agent; and about 34.1 parts (58.2 grams) of polyisocyanate C3 (100 Index). The cyanoalkyl modified siloxane fluid was used in the form of a siloxane fluid-solvent solution composed of about 10 parts by weight of siloxane fluid and 90 parts by weight of solvent S 1. The amount and particular siloxane employed was varied and the recorded properties of the various foam samples are given in TABLE 3 below.

ler shaft was about one-half inch from the bottom of the mixer and the timer set for 12 minutes. The mixture was agitated for 1 minute at 4000 rpm and allowed to

TABLE 3

| Foam No. | Siloxane Fluid No. | Siloxane Solution Conc. (php) | Gurley Foam Breathability | Cells/ Inch | Shrinkage | Cell Uniformity |
|---|---|---|---|---|---|---|
| A | Control | None | 1.9 | 12 | None | Severe Voids - Irregular |
| 1 | II | 0.3 | 6.2 | 22 | None | Slight Voids - Uniform |
| 2 | II | 0.75 | 7.5 | 24 | None | No Voids - Uniform |
| 3 | II | 1.12 | 13.2 | 26 | None | No Voids - Uniform |
| 4 | III | 0.3 | 7.8 | 24 | None | No Voids - Uniform |
| 5 | III | 0.75 | 11.2 | 22 | None | No Voids - Uniform |
| 6 | III | 1.12 | 18.8 | 28 | None | No Voids - Uniform |
| Siloxanes Not of This Invention | | | | | | |
| 7 | XIV | 0.3 | — | — | Severe | No Voids - Uniform |
| 8 | XIV | 0.75 | — | — | Severe | No Voids - Uniform |
| 9 | XV | 0.3 | — | — | Severe | No Voids - Uniform |
| 10 | XV | 0.75 | — | — | Severe | No Voids - Uniform |

EXAMPLE 22

Another series of high resilience polyether urethane foam was produced in molded form by employing 100 parts by weight of a polyether blend on the order of about 60 parts (360 grams) of polyether triol E2 and about 40 parts (240 grams) of polyether triol E3; about 24 cc's. of an aqueous premix of about 2.6 parts of water, about 0.1 part of A1 catalyst, about 1.2 parts of N-ethylmorpholine catalyst and about 0.12 parts of solid triethylenediamine catalyst, along with about 0.3 parts (1.8 cc.) of dibutyltindilaurate catalyst as a five percent solution in S1, and about 34.7 parts (208.2 grams) of polyisocyanate C3. The amount and particular siloxane fluid used was varied as shown by the following table. The procedure followed consisted of weighing out the polyol blend and aqueous amine catalyst premix, heating the prepared mold-release coated aluminum mold to a temperature of about 250°F., then adding the polyol blend and aqueous amine catalyst premix to a 1½ gallon mixing container followed by the required amount of siloxane fluid and dibutyltindilaurate catalyst. The mixing container was placed on a squat baffle assembly and centered so that the propeller shaft was about one-half inch from the bottom of the mixer and the timer set for 12 minutes. The mixture was agitated for 1 minute at 4000 rpm and allowed to degassify (about 25 seconds). Just before the end of degassification the required amount of polyisocyanate was added and the mixing continued for 5 seconds. Upon completion of the mixing the foam forming mixture was rapidly poured into the mold which had been cooled or heated to about 5°F. above the ambient pouring temperature of the mixture. A vented aluminum cover was clamped on to the mold and the mixture was allowed to form, rise and gel and then the clamped mold was then placed in a hot air oven for about 8½ minutes at 300°F. before it was removed and demolded. The recorded properties of the foams so produced are set forth in TABLE 4 below. Siloxane VI was used in the form of a siloxane fluid-solvent solution composed of about 27 parts by weight of siloxane fluid and 73 parts by weight of solvent S1, while Siloxane VII, Siloxane XVI and Siloxane XVII were each used as a solution composed of about 22 parts by weight of siloxane fluid and 78 parts by weight of solvent S1.

TABLE 4

| Foam No. | Siloxane Fluid No. | Siloxane Solution Conc. (php) | Gurley foam Breathability | Shrinkage | Cell Uniformity |
|---|---|---|---|---|---|
| A | — | None | — | None | Severe Voids - Irregular |
| 1 | VI | 0.25 | — | None | Slight Voids - Irregular |
| 2 | VI | 0.5 | 13.4 | None | No Voids - Uniform |
| 3 | VI | 0.75 | 17.8 | None | No Voids - Uniform |
| 4 | VI | 1.5 | 20.7 | None | No Voids - Uniform |
| 5 | VI | 2.25 | 22.7 | None | No Voids - Uniform |
| 6 | VI | 2.5 | — | Slight | No Voids - Uniform |
| 7 | VII | 0.25 | — | None | Slight Voids - Irregular |
| 8 | VII | 0.5 | 17.1 | None | No Voids - Uniform |
| 9 | VII | 0.75 | 19.9 | None | No Voids - Uniform |
| 10 | VII | 1.5 | 20.4 | None | No Voids - Uniform |
| 11 | VII | 2.25 | 24.7 | None | No Voids - Uniform |
| 12 | VII | 2.5 | — | Slight | No Voids - Uniform |
| 13 | XVI | 0.25 | — | None | Slight Voids - Irregular |
| 14 | XVI | 0.5 | 12.8 | None | No Voids - Uniform |
| 15 | XVI | 0.75 | 14.2 | None | No Voids - Uniform |
| 16 | XVI | 1.0 | 16.1 | None | No Voids - Uniform |
| 17 | XVI | 1.5 | 22.4 | None | No Voids - Uniform |
| 18 | XVI | 2.0 | 25.2 | None | No Voids - Uniform |
| 19 | XVI | 2.25 | — | Slight | No Voids - Uniform |
| 20 | XVII | 0.075 | — | None | Slight Voids - Irregular |
| 21 | XVII | 0.125 | 10.1 | None | No Voids - Uniform |
| 22 | XVII | 0.25 | 11.5 | None | No Voids - Uniform |
| 23 | XVII | 0.5 | 12.5 | None | No Voids - Uniform |
| 24 | XVII | 0.75 | 15.1 | None | No Voids - Uniform |
| 25 | XVII | 1.00 | 18.3 | None | No Voids - Uniform |
| 26 | XVII | 1.5 | 22.1 | None | No Voids - Uniform |
| 27 | XVII | 1.75 | 27.1 | Slight | No Voids - Uniform |

EXAMPLE 23

Employing a foam formulation similar to that used in Example 20 a series of high resilience polyether urethane foam was produced in a similar manner using as the cyanoalkyl-modified siloxane fluid, Siloxane XVIII. Foam Nos. 1–5 were based on a laboratory scale-up of ingredients, while Foam Nos. 6–10 were based on a machine scale-up of ingredients. The cyanoalkyl modified siloxane fluid (Siloxane XVIII) was used in the form of a siloxane fluid-solvent solution composed of about 25 parts by weight of siloxane fluid, 57 parts by weight of solvent S1 and 18 parts by weight of a butanol started poly (oxyethylene-oxypropylene) mono- ol diluent having an average molecular weight of about 260 (about 50% by wt. of the oxyalkylene group of the diluent being ethylene oxide units). The amount of siloxane fluid employed was varied and the recorded properties of the various foam samples are given in TABLE 5 below.

TABLE 5

| Foam No. | Siloxane Solution Conc. (php) | Foam Breathability | Cells/Inch | Shrinkage | Cell Uniformity |
|---|---|---|---|---|---|
| 1 | 0.3 | 8.2 | 24 | None | No Voids |
| 2 | 0.7 | 12 | 32 | None | No Voids |
| 3 | 1.0 | 16.8 | 32 | None | No Voids |
| 4 | 1.5 | 22.9 | 34 | None | No Voids |
| 5 | 2.0 | 27.2 | 34 | Slight | No Voids |
| 6 | 0.5 | — | — | None | No Voids |
| 7 | 0.75 | — | — | None | No Voids |
| 8 | 1.0 | — | — | None | No Voids |
| 9 | 1.25 | — | — | None | No Voids |
| 10 | 1.5 | — | — | Slight | No Voids |

EXAMPLE 24

Employing a foam formulation similar to that used in Example 20 a series of high resilience polyether urethane foam was produced in a similar manner using a 50:50 % by weight blend of Siloxane XVIII and Siloxane XIX. Foam Nos. 1–5 were based on a laboratory scale-up of ingredients while Foam Nos. 6–8 were based on a machine scale-up of ingredients. The blend of cyanoalkyl modified siloxane fluids (50 parts by weight of Siloxane XVIII and 50 parts by weight of Siloxane XIX) was used in the form of a siloxane fluid blend-solvent solution composed of about 30 parts of weight of the siloxane fluid blend and 70 parts by weight of solvent S1. The amount of siloxane fluid blend employed was varied and the recorded properties of the various foam samples are given in TABLE 6 below.

TABLE 6

| Foam No. | Siloxane Solution Conc. (php) | Foam Breathability | Shrinkage | Cell Uniformity |
|---|---|---|---|---|
| 1 | 0.35 | 9.4 | None | Moderate Voids |
| 2 | 0.5 | 11.5 | None | No Voids |
| 3 | 0.75 | 16.4 | None | No Voids |
| 4 | 1.25 | 18.9 | None | No Voids |
| 5 | 1.75 | 28.5 | None | No Voids |
| 6 | 0.75 | — | None | No Voids |
| 7 | 2.25 | — | None | No Voids |
| 8 | 2.5 | — | None | No Voids |

The above data in Examples 20–24 demonstrates that the irregular cell structure and voids of the control foams can be eliminated by employing the siloxane fluid stabilizers of this invention without causing any foam shrinkage while siloxane fluids not of this invention were found either to not eliminate the voids of the control foam or to cause foam shrinkage and therefore are not useful as stabilizers in the production of high resilience polyether urethane foam. In cases of slight foam shrinkage the normally smooth regular crown is slightly puckered and wrinkled while in cases of moderate foam shrinkage it is substantially puckered and wrinkled. This surface shrinkage is related to an abnormal quantity of closed cells and tight foam which in turn adversely affects the foams properties such as its resiliency, compression set and load bearing. In cases of severe shrinkage the above defects and disadvantages are even more aggravated and pronounced. In addition severe shrinkage is further evidenced by a pulling away of the foam from the sides and/or bottom of the mold. Thus it is obvious that reasonable amounts of the siloxane fluids of this invention can be employed in the production of high resilience polyether urethane foam whereas such is not the case with the siloxane fluids not of this invention.

Various modifications and variations of this invention will be obvious to a worker skilled in the art and it is to be understood that such modifications and variations are to be included within the purview of this application and the spirit and scope of the appended claims.

What is claimed is:

1. A cyanoalkyl modified siloxane fluid having the average formula

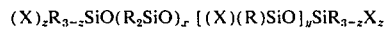

wherein $x$ has a value of 1 to 6 inclusive; $y$ has a value of 0 to 6 inclusive; $z$ has a value of 0 to 1 inclusive; R is a lower alkyl or phenyl radical; and X is a cyanoalkyl radical of the formula $-(O)_nR'CN$ where $n$ has a value of 0 or 1 and R' is an alkylene radical having from 2 to 4 carbon atoms; said siloxane containing at least one of said cyanoalkyl radicals and having an average molecular weight in the range of about 400 to about 1500.

2. A siloxane fluid as defined in claim 1 having an average molecular weight of about 400 to 900, wherein $x$ has a value of 2 to 4 inclusive and $y$ has a value of 1 to 4 inclusive.

3. A siloxane fluid as defined in claim 1 wherein $n$ is 0, $z$ is 0 and R is a lower alkyl radical.

4. A siloxane fluid as defined in claim 3 wherein R is a methyl radical.

5. A siloxane fluid as defined in claim 1 wherein $n$ is 0, $z$ is 1 and R is a lower alkyl radical.

6. A siloxane fluid as defined in claim 5 wherein R is a methyl radical.

7. A siloxane fluid as defined in claim 4 wherein X is a gamma-cyanopropyl radical.

8. A siloxane fluid as defined in claim 2 wherein $n$ is 0, $z$ is 0 and R is a lower alkyl radical.

9. A siloxane fluid as defined in claim 8 wherein R is a methyl radical and X is a gamma-cyanopropyl radical.

10. A siloxane fluid as defined in claim 1 having the average formula

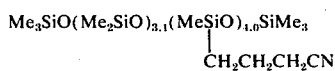

wherein Me is a methyl radical.

11. A siloxane fluid as defined in claim 1 having the average formula

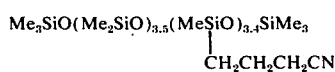

wherein Me is a methyl radical.

12. A siloxane fluid as defined in claim 1 having the average formula

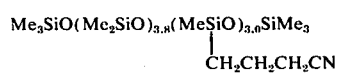

wherein Me is a methyl radical.

13. A siloxane fluid as defined in claim 1 having the average formula

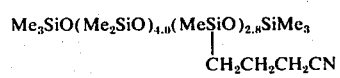

wherein Me is a methyl radical.

14. A siloxane fluid as defined in claim 1 having the average formula

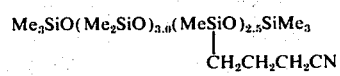

wherein Me is a methyl radical.

15. A siloxane fluid as defined in claim 1 having the average formula

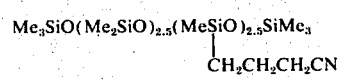

wherein Me is a methyl radical.

16. A siloxane fluid as defined in claim 1 having the average formula

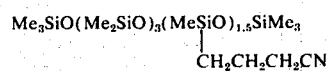

wherein Me is a methyl radical.

17. A siloxane fluid as defined in claim 1 having the average formula

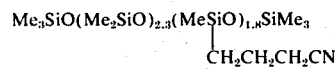

wherein Me is a methyl radical.

18. A siloxane fluid as defined in claim 1 having the average formula

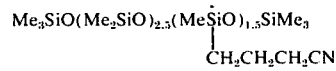

wherein Me is a methyl radical.

19. A siloxane fluid as defined in claim 1 having the average formula

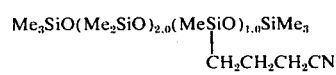

wherein Me is a methyl radical.

20. A siloxane fluid as defined in claim 1 having the average formula

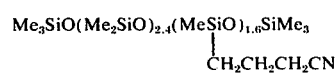

wherein Me is a methyl radical.

21. A siloxane fluid as defined in claim 1 having the average formula

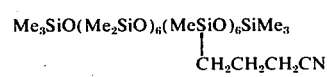

wherein Me is a methyl radical.

22. A siloxane fluid as defined in claim 1 having the average formula

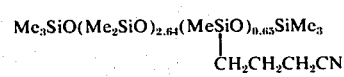

wherein Me is a methyl radical.

23. A siloxane fluid as defined in claim 1 having the average formula

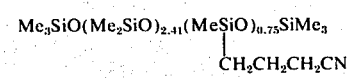

wherein Me is a methyl radical.

24. A siloxane fluid as defined in claim 1 having the average formula

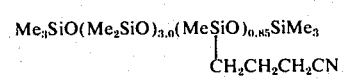

wherein Me is a methyl radical.

25. A siloxane fluid as defined in claim 1 having the average formula

Me$_3$SiO(Me$_2$SiO)$_{2.6}$(MeSiO)$_{1.4}$SiMe$_3$
|
CH$_2$CH$_2$CH$_2$CN wherein Me is a methyl radical.

* * * * *